US011040350B2

(12) United States Patent
Ledden

(10) Patent No.: US 11,040,350 B2
(45) Date of Patent: Jun. 22, 2021

(54) LIQUID ANALYTICAL REAGENT DISPENSING APPARATUS AND ANALYTICAL KITS AND METHODS OF USE RELATED THERETO

(71) Applicant: Siemens Healthcare Diagnostics Inc., Tarrytown, NY (US)

(72) Inventor: David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 259 days.

(21) Appl. No.: 16/317,951

(22) PCT Filed: Jul. 6, 2017

(86) PCT No.: PCT/US2017/040909
§ 371 (c)(1),
(2) Date: Jan. 15, 2019

(87) PCT Pub. No.: WO2018/017332
PCT Pub. Date: Jan. 25, 2018

(65) Prior Publication Data

US 2019/0240667 A1 Aug. 8, 2019

Related U.S. Application Data

(60) Provisional application No. 62/363,567, filed on Jul. 18, 2016.

(51) Int. Cl.
*B01L 3/00* (2006.01)
*G01N 33/48* (2006.01)

(52) U.S. Cl.
CPC ............... *B01L 3/527* (2013.01); *B01L 3/502* (2013.01); *B01L 2200/026* (2013.01);
(Continued)

(58) Field of Classification Search
CPC .. B01L 3/527; B01L 3/502; B01L 2300/0809; B01L 2200/0621;
(Continued)

(56) References Cited

U.S. PATENT DOCUMENTS 5,162,237 A * 11/1992 Messenger .............. B01L 3/502 422/417
5,272,093 A * 12/1993 Silva ....................... B01L 3/505 206/569

(Continued)

FOREIGN PATENT DOCUMENTS

CN 105013546 A 11/2005
CN 1974015 A 6/2007

(Continued)

OTHER PUBLICATIONS

International Search Report and Written Opinion of International Application No. PCT/US2017/040909 dated Sep. 15, 2017.

(Continued)

*Primary Examiner* — Matthew D Krcha
*Assistant Examiner* — Sophia Y Lyle
(74) *Attorney, Agent, or Firm* — Dunlap Codding P.C.

(57) ABSTRACT

Devices, kits, and methods for dispensing at least two liquid reagents for use in analyte(s) detection assays are disclosed.

26 Claims, 8 Drawing Sheets

(52) U.S. Cl.
CPC . *B01L 2200/0621* (2013.01); *B01L 2300/044* (2013.01); *B01L 2300/087* (2013.01); *B01L 2300/0809* (2013.01); *B01L 2400/0406* (2013.01); *B01L 2400/0457* (2013.01)

(58) Field of Classification Search
CPC ......... B01L 2200/026; B01L 2300/044; B01L 2300/087; B01L 2400/0406; B01L 2400/0457
See application file for complete search history.

(56) References Cited

U.S. PATENT DOCUMENTS

| | | | | | |
|---|---|---|---|---|---|
| 5,372,948 | A | * | 12/1994 | Yip | B01L 3/502 422/417 |
| 5,627,041 | A | | 5/1997 | Shartle | |
| 5,805,693 | A | | 9/1998 | Chang et al. | |
| 8,119,067 | B2 | | 2/2012 | Chuang et al. | |
| 2002/0085958 | A1 | | 7/2002 | Nemcek et al. | |
| 2003/0129680 | A1 | | 7/2003 | O'Connor, Jr. | |
| 2003/0166265 | A1 | | 9/2003 | Pugia et al. | |
| 2005/0227360 | A1 | | 10/2005 | Devlin, Sr. | |
| 2009/0093012 | A1 | * | 4/2009 | Bae | B01L 3/502 435/29 |
| 2014/0127828 | A1 | * | 5/2014 | Hou | G01N 33/726 436/501 |
| 2014/0255275 | A1 | | 9/2014 | Barry et al. | |
| 2015/0044764 | A1 | * | 2/2015 | Cha | A61B 5/14546 435/288.7 |
| 2016/0033443 | A1 | | 2/2016 | Ledden | |
| 2018/0193842 | A1 | | 7/2018 | Liu et al. | |

FOREIGN PATENT DOCUMENTS

| | | | | | |
|---|---|---|---|---|---|
| CN | 101308132 | A | | 11/2008 | |
| CN | 101688876 | A | | 3/2010 | |
| CN | 101790349 | A | | 7/2010 | |
| CN | 101876661 | A | | 11/2010 | |
| CN | 101970111 | A | | 2/2011 | |
| CN | 102215965 | A | | 10/2011 | |
| CN | 102871839 | A | | 1/2013 | |
| CN | 203490223 | U | | 3/2014 | |
| CN | 104399540 | A | | 3/2015 | |
| CN | 104582849 | A | | 4/2015 | |
| CN | 105021544 | A | * | 11/2015 | G01N 33/54366 |
| CN | 105021544 | A | | 11/2015 | |
| CN | 105073601 | A | | 11/2015 | |
| CN | 204855520 | U | | 12/2015 | |
| EP | 2546165 | A1 | | 1/2013 | |
| EP | 3318873 | A1 | | 5/2015 | |
| WO | 0165265 | A1 | | 9/2001 | |
| WO | 2008156837 | A1 | | 12/2008 | |

OTHER PUBLICATIONS

European Search Report and Written Opinion of European Application No. 178315602 dated Mar. 25, 2019.

Sun et al., "Non-Contact Submicroliter Liquid Dispensing System with Parameter Adjustment Function", Oct. 2008, Robotics Institute, Harbin Institute of Technology, Optics and Precision Engineering, vol. 16 No. 10, pp. 1913-1921. See English Abstract.

* cited by examiner

LIQUID ANALYTICAL REAGENT DISPENSING APPARATUS AND ANALYTICAL KITS AND METHODS OF USE RELATED THERETO

CROSS REFERENCE TO RELATED APPLICATIONS

The present application claims the benefit of and priority to U.S. Provisional Application Ser. No. 62/363,567, filed Jul. 18, 2016, the entire disclosure of which is incorporated by reference into the present application.

STATEMENT REGARDING FEDERALLY FUNDED RESEARCH OR DEVELOPMENT

Not Applicable.

TECHNICAL FIELD

The presently disclosed and claimed inventive concept(s) relate to a device(s), kit(s), and method(s) for dispensing at least two liquid reagents for use in analyte(s) detection assays. More specifically, the presently disclosed and claimed inventive concept(s) relate to a modified apparatus present within a reaction cassette that is capable of dispensing at least two liquid reagents for use in analyte(s) detection assays, as well as kits and methods of use related thereto.

BACKGROUND

Numerous devices and methods exist for detecting analytes that may be present in a fluid sample. Such devices have been proven to be effective in diagnostic assays that detect the presence and quantity of certain analytes indicative of a patient's health, including, but not limited to, glycated hemoglobin (HbA1c), microalbumin and creatinine, and lipid-based analytes, such as cholesterol, triglycerides, and/or high-density lipoproteins. However, these devices, kits, and methods are limited both in the number and form of reagents that can be employed for the detection of such analytes. Such devices, kits, and methods, for instance, may incorporate a defined number of solid reagents (for example, three solid reagents), but are limited in the number of liquid reagents (for example, one liquid reagent) that can be employed in a given assay(s). Accordingly, a need exists for new and improved devices, kits, and methods that allow for multiple solid reagents and multiple liquid reagents to be used to detect the presence and/or quantity of a specific analyte(s) contained within liquid test sample obtained from a patient. Such devices, kits, and methods thereby allow, by way of example and not by way of limitation, for: (1) an increase in the number of analytes that can be detected in a liquid test sample undergoing a given assay; (2) an increase in assay kinetics associated therewith; (3) enhanced stability due to isolation of potentially incompatible reagents; and (4) the order of reagent addition in the respective assay can be controlled. It is to such devices and methods, as well as kits related thereto, that the presently disclosed and claimed inventive concept(s) is directed.

DETAILED DESCRIPTION

Figure 1A:
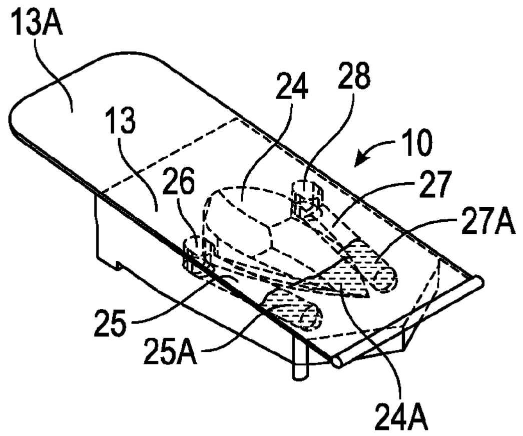
FIG. 1A is detailed perspective views of one embodiment of a liquid analytical reagent dispensing apparatus constructed in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word “a” or “an” when used in conjunction with the term “comprising” in the claims and/or the specification may mean “one,” but it is also consistent with the meaning of “one or more,” “at least one,” and “one or more than one.” The singular forms “a,” “an,” and “the” include plural referents unless the context clearly indicates otherwise. Thus, for example, reference to “a compound” may refer to 1 or more, 2 or more, 3 or more, 4 or more or greater numbers of compounds. The term “plurality” refers to “two or more.” The use of the term “or” in the claims is used to mean “and/or” unless explicitly indicated to refer to alternatives only or the alternatives are mutually exclusive, although the disclosure supports a definition that refers to only alternatives and “and/or.” Throughout this application, the term “about” is used to indicate that a value includes the inherent variation of error for the device, the method being employed to determine the value, or the variation that exists among the study subjects. For example but not by way of limitation, when the term “about” is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term “at least one” will be understood to include one as well as any quantity more than one, including but not limited to, 2, 3, 4, 5, 10, 15, 20, 30, 40, 50, 100, etc. The term “at least one” may extend up to 100 or 1000 or more, depending on the term to which it is attached; in addition, the quantities of 100/1000 are not to be considered limiting, as higher limits may also produce satisfactory results. In addition, the use of the term “at least one of X, Y and Z” will be understood to include X alone, Y alone, and Z alone, as well as any combination of X, Y and Z. The use of ordinal number terminology (i.e., “first”, “second”, “third”, “fourth”, etc.) is solely for the purpose of differentiating between two or more items and is not meant to imply any sequence or order or importance to one item over another or any order of addition, for example.

As used in this specification and claim(s), the terms “comprising” (and any form of comprising, such as “comprise” and “comprises”), “having” (and any form of having, such as “have” and “has”), “including” (and any form of including, such as “Includes” and “include”) or “containing” (and any form of containing, such as “contains” and “contain”) are inclusive or open-ended and do not exclude additional, unrecited elements or method steps.

The term “or combinations thereof” as used herein refers to all permutations and combinations of the listed items preceding the term. For example, “A, B, C, or combinations thereof” is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term “substantially” means that the subsequently described event or circumstance completely occurs or that the subsequently described event or circumstance occurs to a great extent or degree. For example, the term “substantially” means that the subsequently described event or circumstance occurs at least 90% of the time, or at least 95% of the time, or at least 98% of the time.

As used herein, the phrase “associated with” includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term “liquid test sample” as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. The volume of the sample utilized in accordance with the presently disclosed and claimed inventive concept(s) is from about 1 to about 100 microliters. As used herein, the term “volume” as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters.

The term “patient” includes human and veterinary subjects. In certain embodiments, a patient is a mammal. In certain other embodiments, the patient is a human. “Mammal” for purposes of treatment refers to any animal classified as a mammal, including human, domestic and farm animals, nonhuman primates, and zoo, sports, or pet animals, such as dogs, horses, cats, cows, etc.

Turning now to particular embodiments, the presently disclosed and claimed inventive concept(s) relate to a device(s), kit(s), and method(s) for dispensing at least two liquid reagents for use in analyte(s) detection assays. More specifically, the presently disclosed and claimed inventive concept(s) relate to a modified apparatus present within a reaction cassette that is capable of dispensing at least two liquid reagents for use in analyte(s) detection assays, as well as kits and methods of use related thereto.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radioimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radioimmunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbant assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any fluid sample, including, without limitation, whole blood, plasma, serum, or urine.

Referring now to the Figures, and more particularly to FIG. 1A, shown therein is an exemplary embodiment of an apparatus 10 that dispenses liquid analytical reagents which may be used to detect the presence and/or quantity of analytes of interest that may be present in a liquid test sample. The apparatus 10 comprises a container 11 (more specifically shown in FIG. 1B), a flexible cover 13, a first cavity 24 containing a first liquid reagent 24A (which, in one embodiment, may be, for example, assay buffer), a second cavity 25 containing a second liquid reagent 25A, and a third cavity 27 containing a third liquid reagent 27A. While the figures depict embodiments of the container 11 having three cavities (i.e., the first cavity 24, the second cavity 25, and the third cavity 27), it should be readily understood to a person having ordinary skill in the art that the container 11 may be comprised of any number of cavities, provided that the minimum number of liquid reagent cavities and liquid reagents disposed therein is at least two. By way of example and not by way of limitation, the container 11 may comprise 2, 3, 4, 5, 10, 15, 20, 50 or any number of cavities capable of being manufactured for incorporation in container 11. For purposes of clarity only and not by way of limitation, the apparatus 10 shown in the Figures shall be described with reference only the first cavity 24, the second cavity 25, and the third cavity 27.

As shown in FIG. 1A and as further described herein, the flexible cover 13 is removably affixed to the container 11 to seal the container 11, the first cavity 24, the second cavity 25, and the third cavity 27 thereby sealing in and preventing the discharge of the first liquid reagent 24A, the second liquid reagent 25A, and the third liquid reagent 27A from the container 11. The flexible cover 13, when the container 11 is oriented in a substantially vertical position, can be removed by a user to allow the gravitational dispensing of the first liquid reagent 24A from the first cavity 24, but, while a second cavity opening 26 and a third cavity opening 28 are opened by the selective removal of the flexible cover 13, the second liquid reagent 25A and the third liquid reagent 27A remain un-dispensed from the second cavity 25 and the third cavity 27, respectively. The container 11 is preferably fabricated as a molded component formed of a rigid plastic material (so as to avoid deformation of the container 11 upon removal of the flexible cover 13 therefrom by a user), including, for example, high-density polyethylene; however, the container 11 may be constructed of any material capable of accomplishing the presently disclosed and/or claimed inventive concept(s). The flexible cover 13 may be, by way of example only, constructed of a vapor and liquid impermeable material, including, for example, a plastic laminate material or aluminum foil material. In one embodiment, the flexible cover 13 is affixed to the container 11 by a heat-activated peelable adhesive that leaves substantially no residue on the container 11 when the flexible cover 13 is removed by a user. In one embodiment, the flexible cover 13 may be constructed and configured to comprise a pull tab portion 13A, which can be grasped and pulled by a user to remove the flexible cover 13 from the container 11.

Figure 1B:
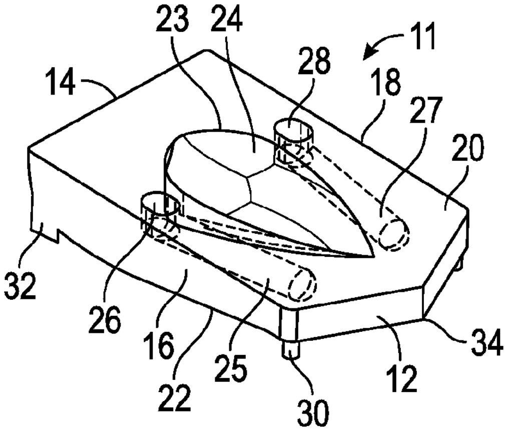
FIG. 1B is a detailed perspective view of one embodiment of the opened container (without the flexible cover) of the presently disclosed and/or claimed inventive concept(s).

Referring now to FIG. 1B, shown therein is an exemplary embodiment of the container 11 in which the flexible cover 13 has been removed from the container 11 and in which the first liquid reagent 24A, second liquid reagent 25A, and third liquid reagent 27A are not present. As shown in FIG. 1B, the container 11 comprises a first end 12, a second end 14, a first side 16, a second side 18, a top side 20, a bottom side 22, and a flange 23 extending around the open top of the first cavity 24. The container 11 may also comprise at least one first support 30 and at least one second support 32 such that when the container 11 is oriented in a substantially vertical position, the at least one first support 30 and the at least one second support 32 may engage and abut a surface so as to stabilize the orientation of the container 11 in the substantially vertical position. In one embodiment, the at least one first support 30 is shorter in length than the at least one second support 32 such that the container 11, when positioned in a substantially vertical position, is positioned at an angle to facilitate the dispensing and/or directional flow of at least the first liquid reagent 24A. The container 11 may also be shaped in such a configuration so as to include an apex 34, although it should be understood by a person having ordinary skill in the art that the container 11 can be configured and shaped in any manner that accomplishes the presently disclosed and/or claimed inventive concept(s). When apex 34 is present, apex 34 facilitates the directional flow of liquid reagent(s) dispensed from the first cavity 24, the second cavity 25, and/or the third cavity 27 of the container 11.

Figure 2:
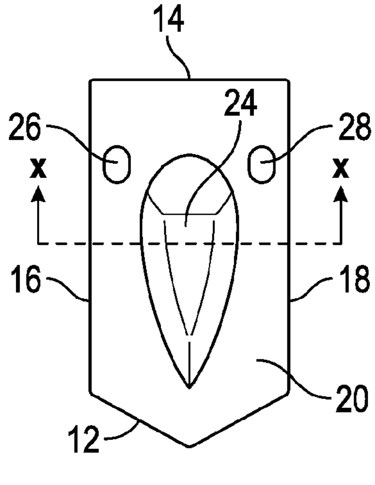
FIG. 2 is a top view of one embodiment of the opened container (without the flexible cover) of the presently disclosed and/or claimed inventive concept(s).
Figure 3:
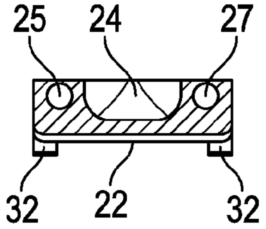
FIG. 3 is a cross-sectional view of one embodiment of the opened container as viewed from the perspective of line x as shown in FIG. 2.

As shown in FIGS. 1B and 2, the container 11, by way of example and not by limitation, includes the second cavity opening 26 and the third cavity opening 28. While the second cavity opening 26 and the third cavity opening 28 are shown in the Figures as being located on the top side 20 of the container 11 near the second end 14 and on opposing sides of the first cavity 24, it should be understood by a person having ordinary skill in the art that the second cavity opening 26 and the third cavity opening 28 can be located on any portion of the container 11 that accomplishes the presently disclosed and/or claimed inventive concept(s). The second cavity opening 26, in accordance with the presently disclosed and/or claimed method(s), allows for the selective dispensing of the second liquid reagent 25A from the second cavity 25 of the container 11. Likewise, the third opening 28 allows for the selective dispensing of the third liquid reagent 27A from the third cavity 27 of the container 11.

Referring now to FIGS. 3-7, in one embodiment, the second cavity 25 and the third cavity 27 are, by way of example, formed on the bottom side 22 of the container 11. However, it should be understood to a person having ordinary skill in the art that the second cavity 25 and the third cavity 27 may be formed on any portion of the container 11 capable of accomplishing the presently disclosed and/or claimed inventive concept(s), including, without limitation, on the top portion 20, the first side 16, and/or the second side 18 of container 11. In one embodiment, the second cavity 25 and third cavity 27 are substantially cylindrical in shape with a closed end located longitudinally opposite from the second cavity opening 26 and the third cavity opening 28, respectively. However, it should be readily understood to a person having ordinary skill in the art that while the second cavity 25 and third cavity 27 are shown in the Figures as being substantially cylindrical in shape, the second cavity 25 and the third cavity 27 may be of any shape capable of retaining and selectively dispensing the second liquid reagent 25A and the third liquid reagent 27A, respectively, including, but not limited to triangular, pentagonal, hexagonal, heptagonal, octagonal, or any other shape capable of accomplishing the presently disclosed and/or claimed inventive concept(s). In addition, while the second cavity 25 and the third cavity 27 are shown in the Figures as being the same shape, it should be understood to a person having ordinary skill in the art that the second cavity 25 and the third cavity 27 may be different in shape.

Figure 4:
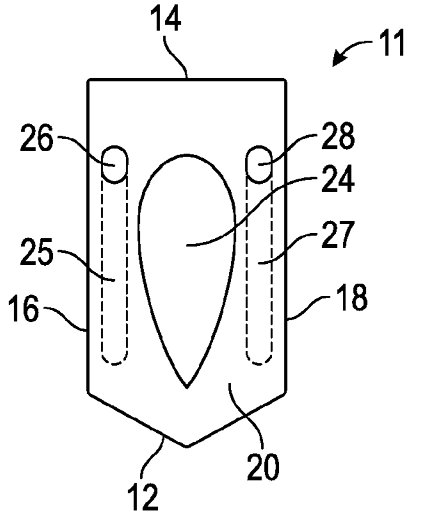
FIG. 4 is a top view of one embodiment of the opened container constructed in accordance with the presently disclosed and/or claimed inventive concept(s).
Figure 5:
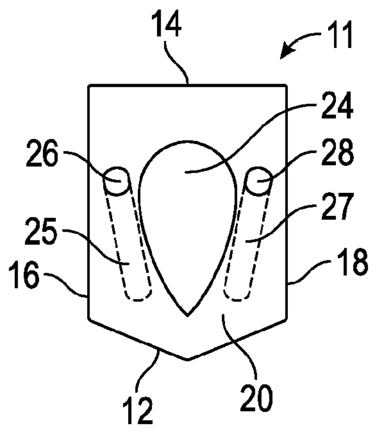
FIG. 5 is a top view of an alternative embodiment of the opened container constructed in accordance with the presently disclosed and/or claimed inventive concept(s).
Figure 6:
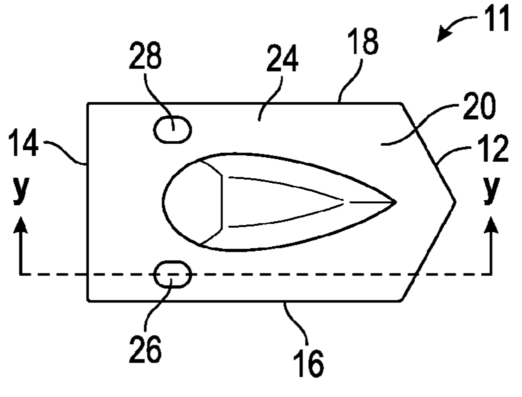
FIG. 6 is a top view of one embodiment of the opened container constructed in accordance with the presently disclosed and/or claimed inventive concept(s).
Figure 7:
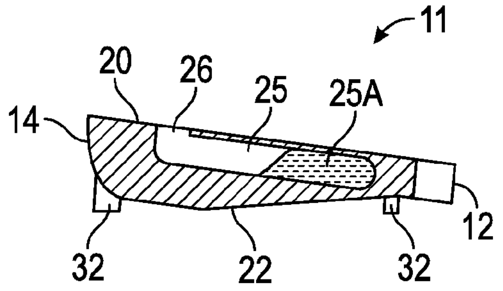
FIG. 7 is a cross-sectional view of one embodiment of the opened container as viewed from the perspective of line y as shown in FIG. 6.

As shown more specifically in FIGS. 4-5, in one embodiment, the second cavity 25 and the third cavity 27 are positioned on opposing sides of the first cavity 24 extending longitudinally from the second end 14 to the first end 12 of the container 11, with the second cavity opening 26 being positioned near the first side 16 of the container 11 and the third cavity opening 28 being positioned near the second side 18 of the container 11. In one embodiment, the second cavity opening 26 and the third cavity opening 28 are located on the top side 20 of the container 11 near the second end 14 while the second cavity 25 and the third cavity 27 are formed on the bottom side 22 of the container 11 and extend longitudinally from the second end 14 to the first end 12 of the container 11. In one embodiment, the second cavity 25 and the third cavity 27 are configured to be parallel along a longitudinal axis extending from the second end 14 to the first end 12 of the container 11. In another embodiment, the second cavity 25 and the third cavity 27 are configured at an angle along a longitudinal axis extending from the second end 14 to the first end 12 of the container 11. In this embodiment, the second cavity 25 and the third cavity 27 are located on the bottom side 22 of the container on opposite sides of the first cavity 24 (with the second cavity 25 being located near the first side 16 of the container 11 and the third cavity being located near the second side 18 of the container 11). Further, in this embodiment, the second cavity 25 and third cavity 27 angle away from a longitudinal axis extending from the second end 14 to the first end 12 of the container 11. While certain embodiment of the second cavity 25 and the third cavity 27 are shown in the Figures as being substantially parallel and/or angled with respect to a longitudinal axis extending from the second end 14 to the first end 12 of the container 11, it is readily understood to a person having ordinary skill in the art that the second cavity 25 and the third cavity 27 can be positioned in any orientation that accomplishes the presently disclosed and/or claimed inventive concept(s). Additionally, for the embodiment in which the second cavity 25 and the third cavity 27 are angled with respect to the longitudinal axis, the angles related thereto can be of any degree in order to accomplish the presently disclosed and/or claimed inventive concept(s), including, by way of example and not by way limitation, 1°, 2°, 5°, 10°, 15°, 20°, 25°, 30°, 35°, 40°, 45°, 50°, 55°, 60°, 65°, 70°, and 75°. In addition, the second cavity 25 and the third cavity 27 may each be coated with either a hydrophilic or hydrophobic composition (not shown) to decrease or increase, respectively, the ease in which the second liquid reagent 25A is dispensed from the second cavity 25 or the third liquid reagent 27A is dispensed from third cavity 27. In one embodiment, the second cavity 25 and the third cavity 27 are oriented such that when the container 11 is rotated about a substantially horizontal axis, the second liquid reagent 25A disposed within the second cavity 25 and the third liquid reagent 27A disposed within the third cavity 27 are simultaneously dispensed into the reaction chamber 56 of the reaction cassette 41 (discussed below and illustrated in FIGS. 8-10) via the second cavity opening 26 and the third cavity opening 28, respectively. In an additional embodiment, the second cavity 25 and the third cavity 27 are oriented such that when the container 11 is rotated about a substantially horizontal axis, the second liquid reagent 25A disposed within the second cavity 25 and the third liquid reagent 27A disposed within the third cavity 27 are sequentially and controllably dispensed into the reaction chamber 56 of the reaction cassette 41 (discussed below) via the second cavity opening 26 and the third cavity opening 28, respectively. In this latter embodiment, the sequential and controlled addition of the second liquid reagent 25A and the third liquid reagent 27A may be facilitated, for example, by the angled configuration of the second cavity 25 and the third cavity 27 with respect to the longitudinal axis as described herein and/or the coating of the inner portions of the second cavity 25 and the third cavity 27 with a hydrophilic (i.e., decreases the flow of the liquid reagent(s)) and/or hydrophobic (i.e., increases the flow of the liquid reagent(s)) composition(s).

Figure 8:
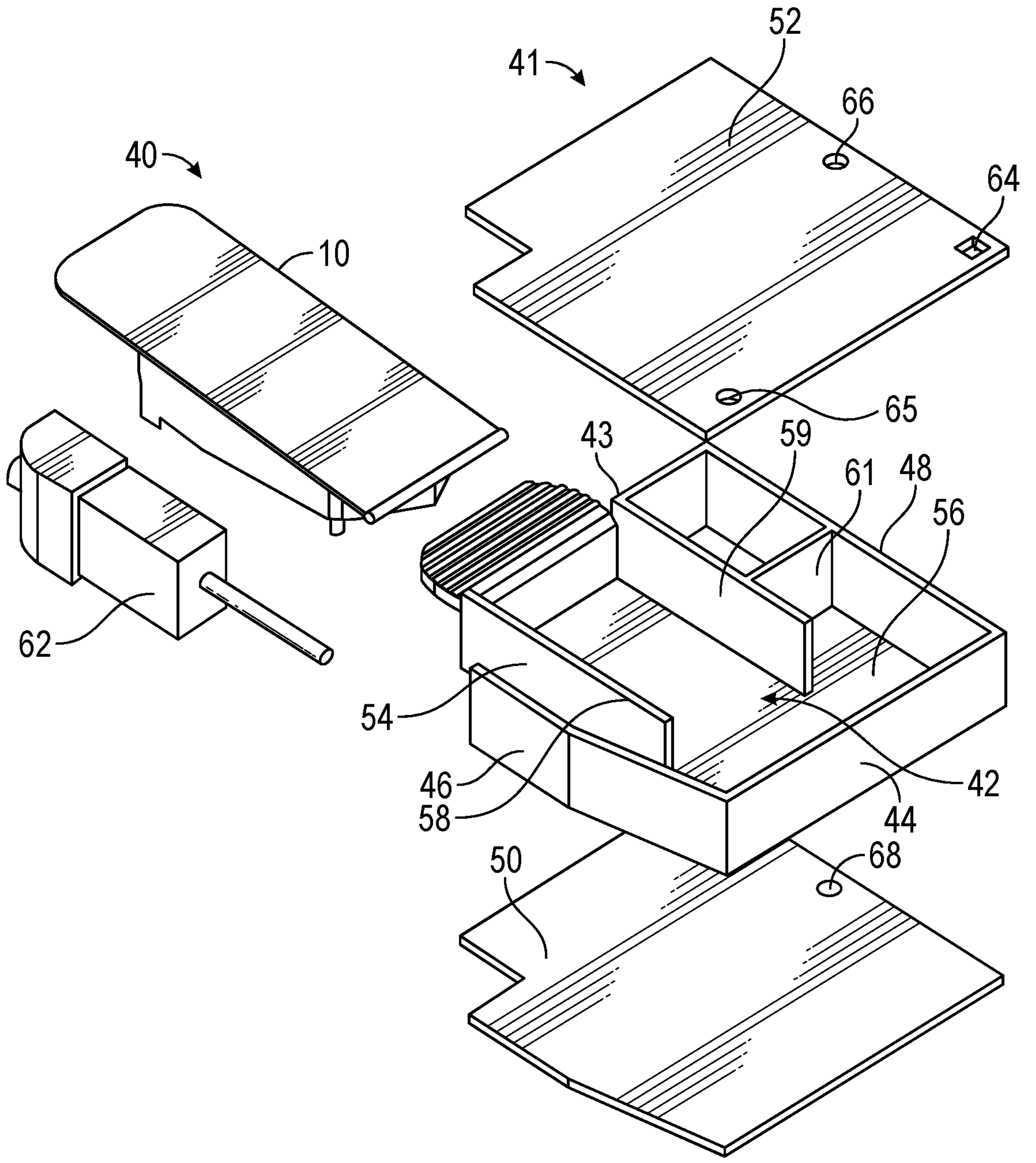
FIG. 8 is an exploded perspective view of one embodiment of an analytical reaction kit constructed in accordance with presently disclosed and/or claimed inventive concept(s).

Referring now to FIG. 8, shown therein is one embodiment of an analytical research kit 40. The analytical research kit 40 comprises the apparatus 10, a reaction cassette 41, and a capillary 62, used for obtaining a liquid reaction sample from a patient and introducing such sample into the reaction cassette 41.

The apparatus 10 is constructed in accordance with the previous description provided and in accordance with the presently disclosed and/or claimed inventive concept(s).

The reaction cassette 41 comprises a body 42 formed by the top perimeter side 43, a bottom perimeter side 44, a first perimeter side 46, a second perimeter side 48, and a bottom portion 50. The reaction cassette 41 further comprises a top portion 52 that is used to seal the body 42 of the reaction cassette 41 after the apparatus 10 containing the liquid analytical reagents has been incorporated into the reaction cassette 41 as described and/or claimed herein. Such seal can be accomplished via any method commonly known in the art, including, without limitation, adhesive(s), glue, sonic welding, laser welding, and/or any permanent fastener(s).

In one embodiment, the body 42 of the reaction cassette 41 is constructed such that the body is formed via the connection of the top perimeter side 43, the bottom perimeter side 44, the first perimeter side 46, and the second perimeter side 48 to the bottom portion 50. Such connection can be via any method commonly known in the art, including, without limitation, adhesive(s), glue, sonic welding, laser welding, and/or any permanent fastener(s). In another embodiment, the body 42 can be constructed such that the top perimeter side 43, the bottom perimeter side 44, the first perimeter side 46, the second perimeter side 48, and the bottom portion 50 is one contiguous piece, for instance, by way of example only, one contiguous piece of plastic.

The reaction cassette 41 has a substantially horizontal axis of rotation. While the external dimensions of the reaction cassette 41 are not critical, the reaction cassette 41 typically has a height and width of about 3 centimeters to about 15 centimeters and a thickness of about 0.25 centimeters to about 2 centimeters. In one embodiment, the dimensions of the reaction cassette 41 are a height and width of about 6 centimeters and a thickness of about 1 centimeter.

The body 42 of the reaction cassette 41 further comprises a first inner wall 58 and a second inner wall 59, wherein the first inner wall 58 and the second inner wall 59 extend downward from the top perimeter side 43 and are positioned opposite of one another and substantially perpendicular to the top perimeter side 43 and the bottom perimeter side 44. The first perimeter side 46, together with the second perimeter side 48, the bottom portion 50, and the top portion 52 form a reaction chamber 56, a portion of which is U-shaped and formed by a third inner wall 61 which extends between and substantially perpendicular to the second inner wall 59 and the second perimeter side 48. Once the body 42 of the reaction cassette 41 has been sealed by the top portion 52 following the incorporation of apparatus 10 into the reaction cassette 41, an inlet 54 is thereby formed between the first perimeter side 46 and the first inner wall 58, the inlet 54 being substantially parallel to the first perimeter side 46 and the first inner wall 58 and extending from top perimeter side 43 downward toward the bottom perimeter side 44 of the reaction cassette 41. The inlet 54 is capable of securely receiving the capillary 62 such that the liquid test sample (not shown) is introduced from the capillary 62 into the reaction chamber 56 of the reaction cassette 41. While a capillary 62 is shown in the Figures as introducing the liquid test sample (not shown) into the reaction chamber 56 of the reaction cassette 41, it should be readily understood to a person having ordinary skill in the art that the liquid test sample (not shown) can be introduced into the reaction cassette 41 via any device capable of introducing a liquid a test sample, including, by way of example and not by way of limitation, a pipette(s). In addition, the inlet 54 can be stoppered, plugged, or otherwise closed subsequent to the introduction of the liquid test sample into the reaction cassette 41 so as to prevent liquid loss during the course of the methodologies described herein, including, but not limited to, assays, including immunoassays.

Figure 9:
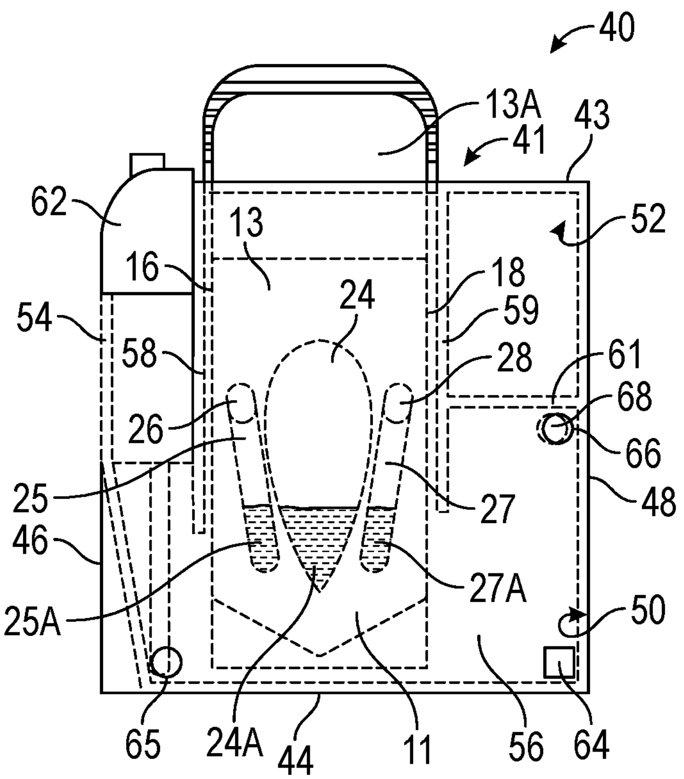
FIG. 9 is a top view of one embodiment of the analytical reaction kit constructed in accordance with the presently disclosed and/or claimed inventive concept(s).

Referring now to FIG. 9, shown therein is one embodiment of the analytical reaction kit 40 which comprises the apparatus 10 which has been incorporated into the reaction cassette 41 and the capillary 62 which has been securely received into the inlet 54 of the reaction cassette 41. As shown in the FIG. 9, the apparatus 10 remains closed and sealed by the flexible cover 13 thereby sealing in the first liquid reagent 24A within the first cavity 24, the second liquid reagent 25A within the second cavity 25, and the third liquid reagent 27A within the third cavity 27. In one embodiment, the container 11 is affixed within the reaction cassette 41 whereby the container 11 is positioned so as to secure between the first inner wall 58 and the second inner wall 59, such that the first side 16 of the container 11 is oriented substantially parallel to the first inner wall 58 of the reaction cassette 41 and the second side 18 of the container 11 is oriented substantially parallel to the second inner wall 59, wherein the at least one first support 30 (not shown) and the at least one second support 32 (not shown) abut and/or are affixed to the bottom portion 50 of the reaction cassette 41. The first perimeter side 46, together with the second perimeter side 48, the bottom portion 50, and the top portion 52 form a reaction chamber 56, a portion of which is U-shaped and formed by a third inner wall 61 which extends between and substantially perpendicular to the second inner wall 59 and the second perimeter side 48. The reaction chamber 56 is in liquid communication with the inlet 54, thereby allowing a liquid test sample (not shown) to be introduced via the capillary 62 into the reaction chamber 56 of the reaction cassette 41.

In one embodiment and as shown in FIGS. 8 and 9, positioned along the reaction chamber 56 is a sample read window 64, a first solid reagent zone 65, a second solid reagent zone 66, and a third solid reagent zone 68. While shown in the Figures as comprising three individual solid reagent zones, it should be understood to a person having ordinary skill in the art, that any number of solid reagent zones may be used (or may be totally absent from reaction cassette 41) and positioned at any location(s) along the reaction chamber 56 in order to accomplish the presently disclosed and/or claimed inventive concept(s). The sample read window 64 can be, by way of example only and not by way of limitation, a transparent cuvette window or an optical window which permits the accurate measurement of detectable signals in the area of the sample read window 64. In one embodiment, the first solid reagent zone 65 is substantially located at a corner of the reaction cassette 41 formed from the perpendicular intersection of the first perimeter side 46 and the bottom perimeter side 44 wherein the first solid reagent zone 65 is formed on the top portion 52 of the reaction cassette 41. In one embodiment, the second solid reagent zone 66 and the third solid reagent zone 68 are substantially located at a corner of the reaction cassette 41 formed from the perpendicular intersection of the second perimeter side 48 and the third inner wall 61 wherein the second solid reagent zone 66 is formed on the top portion 52 of the reaction cassette 41 and the third solid reagent zone 68 is formed on the bottom portion 50 of the reaction cassette 41. When present, the solid reagent zones 65, 66, and 68 are incorporated with solid analytical reagents for performing a particular analytical assay procedure. The solid analytical reagents are, in one embodiment, present in the solid reagent zones in a substantially dry, water soluble, suspendable or dissolvable form, and can be incorporated along the reaction chamber 56 according to methods known in the art, such as, for example, by noncovalent binding techniques, absorptive techniques, and the like, in the desired order in which they are to be sequentially contacted with a liquid test sample. In one embodiment, the solid reagent zones 65, 66, and 68, when present, are defined in the form of substantially flat, raised portions or mesa-shaped nodes on the surface of the selected area of the reaction chamber 56, in which the raised upper surface of each node is from about 0.005 inches to about 0.02 inches elevated above a surface of the reaction chamber 56.

In accordance with the above, in one embodiment, the reaction cassette 41 may comprise three liquid reagents (which are present and selectively contained within the first cavity 24, the second cavity 26, and the third cavity 27 of the container 11, respectively) and three solid reagents for accomplishing the presently disclosed and/or claimed inventive concept(s), including, without limitation, assays, including immunoassays. In one embodiment, the first solid reagent zone 65 comprises an oxidant (such as, for example, ferricyanide), while the second solid reagent zone 66 and the third solid reagent zone 68 comprise an agglutinator and an antibody-latex (for instance, by way of example only, a glycated hemoglobin A1c antibody), respectively. However, it should be readily understood to a person having ordinary skill in the art, that any compound, composition, and/or molecule can be used on the solid reagent zones in order to accomplish the presently disclosed and/or claimed inventive concept(s), including, without limitation, detection of at least one analyte(s) of interest present in a liquid test sample. In addition, it should be understood to a person having ordinary skill in the art that the presently disclosed and/or claimed inventive concept(s) can be accomplished in the absence of any or all of the first solid reagent zone 65, the second solid reagent zone 66, and the third solid reagent zone 68. In such an instance, the first liquid reagent 24A, the second liquid reagent 25A, and/or the third liquid reagent 26A are capable of detecting at least one analyte(s) present in a liquid test sample in the absence of one or all of the solid reagent zones 65, 66, and/or 68.

Referring now to FIGS. 10A-10F, shown therein is one embodiment of an analytical research kit 40 constructed in accordance with the presently disclosed and/or claimed inventive concept(s) being used in a method of the presently disclosed and/or claimed inventive concept(s) to detect at least one analyte(s) of interest present in a liquid test sample. While FIGS. 10A-10D show a first solid reagent zone 65, a second solid reagent zone 66, and a third solid reagent zone 68, as described above, the presently disclosed and/or claimed inventive concept(s) can be accomplished via use of the first liquid reagent 24A, the second liquid reagent 25A, and the third liquid reagent 27A. Accordingly, the methodology(-ies) described in these Figures is with reference only to the liquid reagents 24A, 25A, and 27A; however, it should be understood to a person having reasonable skill in the art that presently disclosed and/or claimed methodology(-ies) may be accomplished via a combination of any number of solid reagents (present on solid reagent zones) and liquid reagents. The analytical research kit 40 is shown in various rotational positions to further illustrate the gravitational flow and mixing of the liquid test sample (not shown), the first liquid reagent 24A, the second liquid reagent 25A, and the third liquid reagent 27A along the reaction chamber 56 as the analytical research kit 40 is rotated about the substantially horizontal axis. The solid arrows shown outside of the analytical research kit 40 indicate the direction of rotation of the analytical research kit 40 about the horizontal axis.

It is to be understood that FIGS. 10A-10F are for purposes of illustration only and are not intended to limit the number, nature, or manner of incorporation of analytical reagents (solid and/or liquid) into the analytical research kit 40, or the sequence or direction of rotation of the analytical research kit 40. For example, and as described hereinabove, although three solid assay reagent zones 65, 66, and 68 and three liquid reagents 24A, 25A, and 27A are shown, other assay procedures, including, but not limited to immunoassays procedures, and, more specifically, immunoturbidimetric assay procedures, can also be performed in the analytical research kit 40 in which the number of analytical reagents (solid and/or liquid) may vary depending on the particular assay requirements. In addition, the analytical research kit 40 may include less than the required number of analytical reagents (solid and/or liquid) for performing an analytical assay procedure where one or more reaction mixtures thereof can first be performed outside of the analytical research kit 40 and then introduced into the analytical research kit 40 to complete the assay.

An illustrative, non-limiting method of using the analytical research kit 40 depicted in FIGS. 8-9 will now be described as shown in FIGS. 10A-10F. As shown in these Figures, the flexible cover 13 has been removed, thereby allowing the gravitational dispensing and flow of the first liquid reagent 24A from the first cavity 24, while the second liquid reagent 25A and the third liquid reagent 27A remain disposed within the second cavity 25 and the third cavity, respectively. However, it should be understood to a person having ordinary skill in the art that the flexible cover 13 is present upon insertion of the reaction cassette 41 into the suitable instrument, apparatus, or system and is selectively removed at the appropriate time (as described below) by a user during the conducting of the assay test. As discussed herein, the various rotation and oscillation movements of the analytical research kit 40 can be performed manually, but in most cases will be performed by a suitable instrument, apparatus, or system, including, without limitation, the DCA Vantage® Analyzer commercially available from Siemens Healthcare Diagnostics, Inc. Additionally, while the presently disclosed methodology(-ies) as shown in FIGS. 10A-10F depict the sequential addition of liquid reagents, it should be understood to a person having reasonable skill in the art that, in an alternative embodiment, the analytical reaction kit 40 can be rotated such that all of the liquid reagents or selected liquid reagents are simultaneously dispensed into the reaction chamber 56. Similarly, in additional embodiments of the presently disclosed and/or claimed inventive concept(s), the container 11 can be constructed in a manner such that the second liquid reagent 25A and the third liquid reagent 27A are simultaneously released into the reaction chamber 56 with the first liquid reagent 24A upon the removal of the flexible cover 13 from the container 11. In another embodiment, as depicted in FIGS. 11A and 11B, the second liquid reagent 25A may be released simultaneously with the first liquid reagent 24A into the reaction chamber 56 upon the removal of the flexible cover 13, while the third liquid reagent 27A remains in the third cavity 27 for later release. The mixture of the first liquid reagent 24A and the second liquid reagent 25A can then be utilized to carry out the various assay methodology(-ies) described and/or claimed by the presently disclosed inventive concept(s). Likewise, in another embodiment of the presently disclosed and/or claimed inventive concept(s), the third liquid reagent 27A is released simultaneously with the first liquid reagent 24A into the reaction chamber 56 upon the removal of the flexible cover 13, while the second liquid reagent 25A remains in the second cavity 25 for later release. The mixture of the first liquid reagent 24A and the third liquid reagent 27A can then be utilized to carry out the various assay methodology(-ies) described and/or claimed by the presently disclosed inventive concept(s).

In one embodiment, the first step is to provide the reaction cassette 41 into a holder mechanism of the above-referenced instrument, apparatus, or system such that a second corner 74 of the reaction cassette 41, which is formed by the substantial perpendicular intersection of the second perimeter side 48 and the bottom perimeter side 44, is positioned in a downward orientation. Following insertion of the reaction cassette 41 into the suitable instrument, apparatus, or system, a liquid test sample (not shown) is drawn into the capillary 62 and the capillary 62 containing the liquid test sample is inserted into inlet 54 whereby the liquid test sample contained in the capillary 62 is proximally located near a first corner 72 of the reaction cassette 41. Upon insertion of the capillary 62 into the inlet 54 of the reaction cassette 41, the capillary 62 seals the inlet 54 of the reaction cassette 41, thereby forming the analytical reaction kit 40. The portion of the capillary 62 near the first corner 72 is preferably configured as shown such that when the capillary 62 is positioned as described above, the portion of the capillary 62 containing the liquid test sample is capable of being efficiently contacted by a liquid in the reaction chamber 56, such as the first liquid reagent 24A, the second liquid reagent 25A, and/or the third liquid reagent 27A which may be introduced into the reaction chamber 56 from the first cavity 24, the second cavity 25, and/or the third cavity 27, respectively.

Figure 10A:
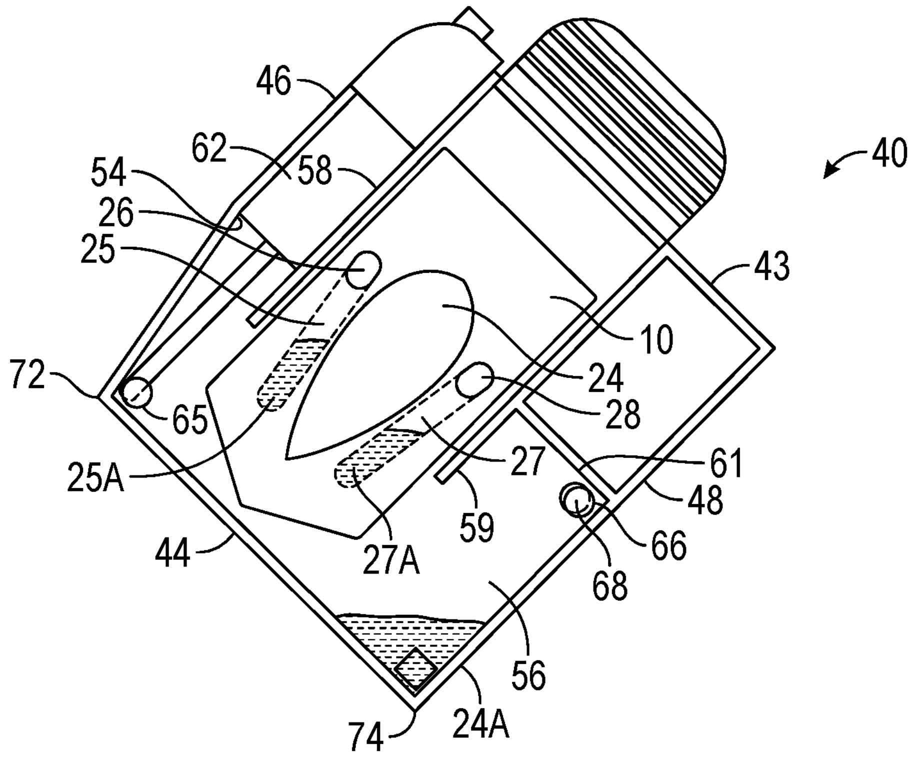
FIGS. 10A-10F are top views of one embodiment of the analytical reaction kit being used for the detection of at least one analyte present in a liquid test sample in accordance with the methodologies disclosed and/or claimed herein.
Figure 11A:
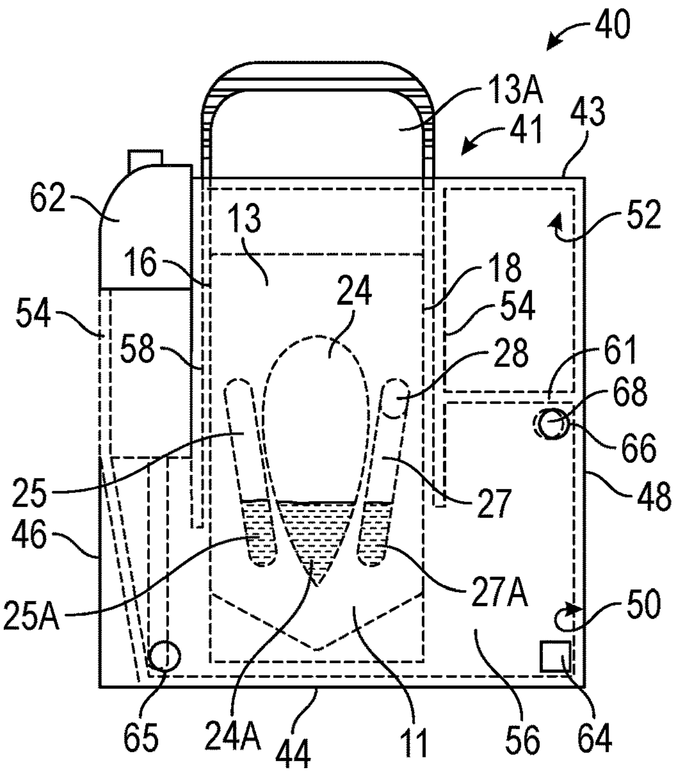
FIGS. 11A-11B are top views of another embodiment of the analytical reaction kit being used for the detection of at least one analyte present in a liquid test sample in accordance with the methodologies disclosed and/or claimed herein.
Figure 11B:
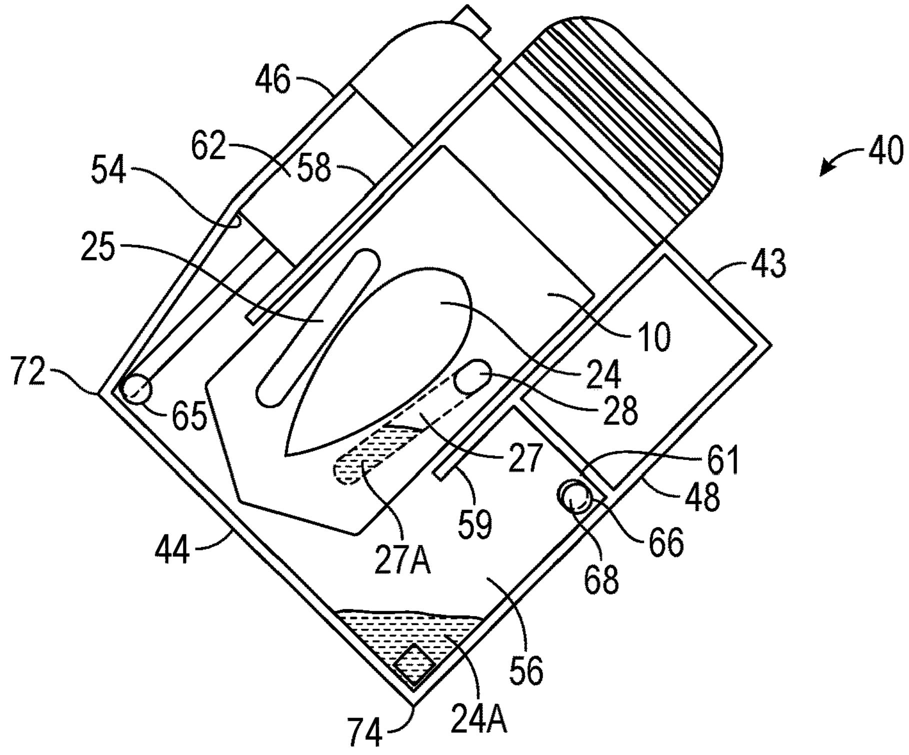

As shown in FIG. 10A, the first liquid reagent 24A contained within the first cavity 24 is introduced into the reaction chamber 56 by pulling the pull tab portion 13A of the flexible cover 13 (not shown) in a direction away from the analytical research kit 40 (as shown by the solid arrow in FIG. 9). The first liquid reagent 24A (which, for example, may be a non-reactive buffer solution) is freely dispensed and flows by gravity along the path shown by the broken arrow in FIG. 10A into the second corner 74 of the reaction chamber 56. A blank absorbance reading can be taken through the sample read window 64 at the starting position with the second corner 74 oriented downward.

Figure 10B:
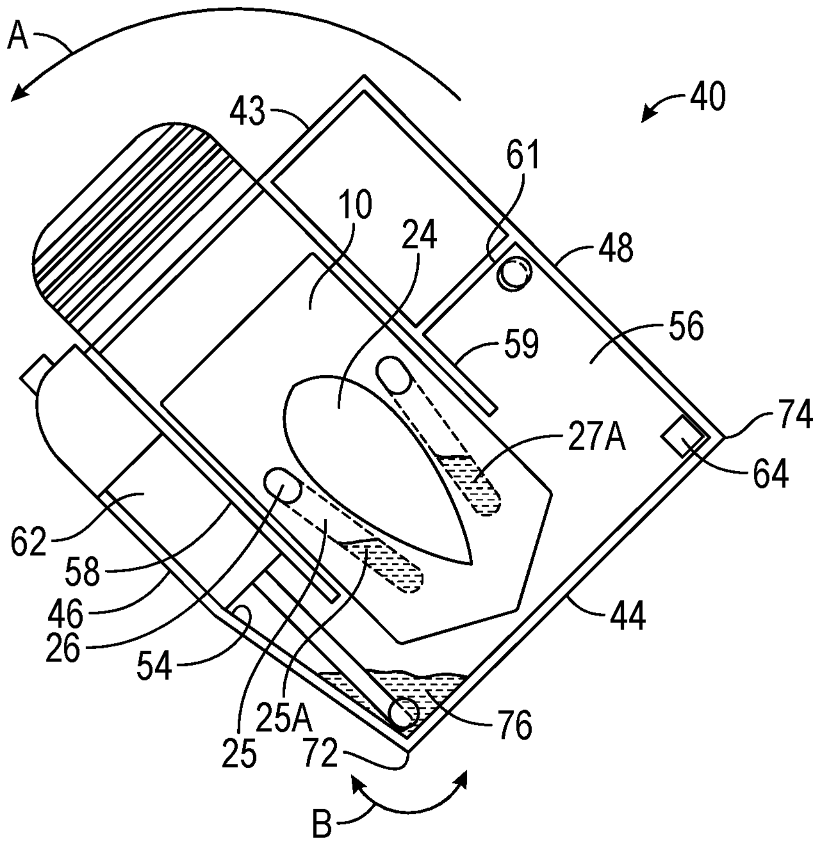
Figure 10C:
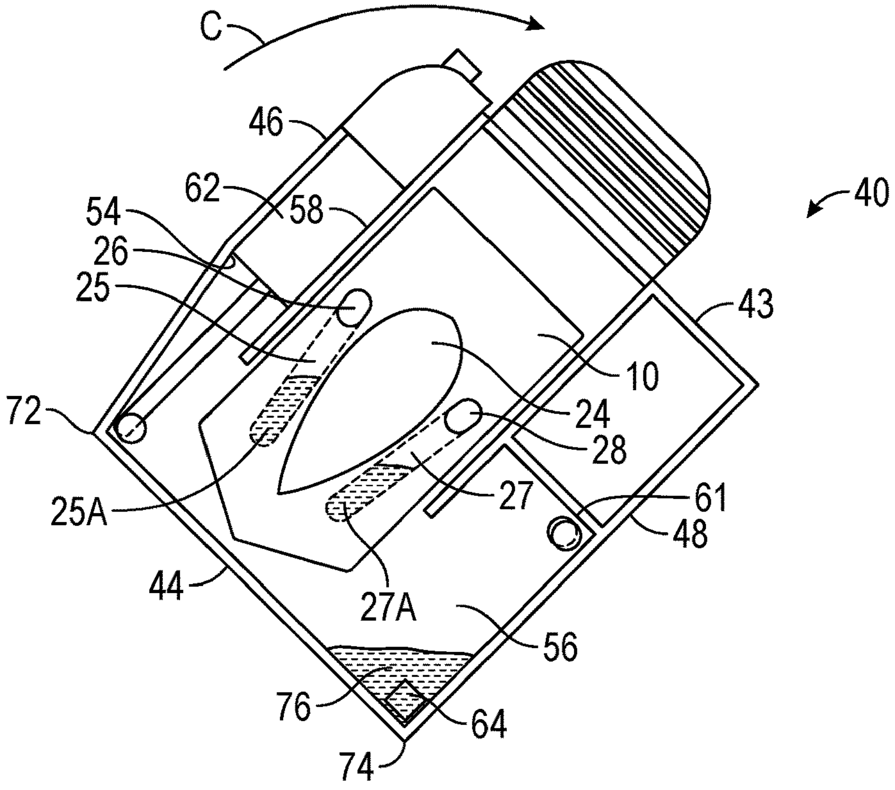

As shown in FIG. 10B, the analytical research kit 40 may then be rotated in a counter-clockwise direction (as shown by solid directional arrow A) and oscillated (as shown by solid arrow B) whereby the first liquid reagent 24A is transported by gravity along the reaction chamber 56 (shown by the broken arrow in FIG. 10B) from the second corner 74 and brought into contact with the first corner 72 and the portion of the capillary 62 containing the liquid test sample (not shown). As shown therein, the second liquid reagent 25A and the third liquid reagent 27A remain disposed within the second cavity 25 and the third cavity 27, respectively; at this step (and oscillation associated therewith and described below), the degree of rotation of the analytical research kit is sufficient to transport the first liquid reagent 24A from the second corner 74 to the first corner 72, it is insufficient to release either the second liquid reagent 25A or the third liquid reagent 27A into the reaction chamber 56. It is to be understood that, in accordance with the presently disclosed and/or claimed inventive concept(s) the turbulence caused by the first liquid reagent 24A impacting the first corner 72 during oscillation of the analytical research kit 40 results in the removal of the liquid test sample from the capillary 62 to form a first reaction mixture 76. In addition, in the presence of the first solid reagent zone 65, the oscillation allows for the solubilization of the solid analytical reagent present on the first solid reagent zone 65 by the first liquid reagent 24A. The analytical research kit 40 can be maintained in a stationary position for a predetermined amount of time to allow the at least one analyte(s) present in the first reaction mixture 76 to sufficiently interact and/or associate with the first liquid reagent and/or the solid analytical reagent (when the first solid reagent zone 65 is present in the analytical research kit 40).

Where the first reaction mixture 76 provides a first detectable response or measureable characteristic which is required or desired to be measured according to a particular assay protocol, as shown in FIG. 10C, the analytical research kit 40 is rotated (the angle of which is not great enough to dispense the second liquid reagent 25A and/or the third liquid reagent 27A) in a clockwise direction (as shown by the solid directional arrow C) such that the first reaction mixture 76 is transported by gravity to the sample read window 64 in the second corner 74, and the analytical research kit 40 is maintained in a stationary position. Any such first detectable response provided by the first reaction mixture 76 can then be measured, and the remaining assay steps, if necessary, can be carried out subsequent thereto. By way of example only and not by way of limitation, the first detectable response may be a total hemoglobin measurement where the liquid test sample is whole blood, for example, such as when performing an assay for the percent of glycated hemoglobin (HbA1c) in a whole blood sample. In the case of a lipid-based assay, the first detectable response may be total cholesterol measurement where the liquid test sample is blood serum, for example, when performing an assay for the calculation of the percent of low-density lipoprotein (LDL) cholesterol present in a blood serum sample.

Figure 10D:
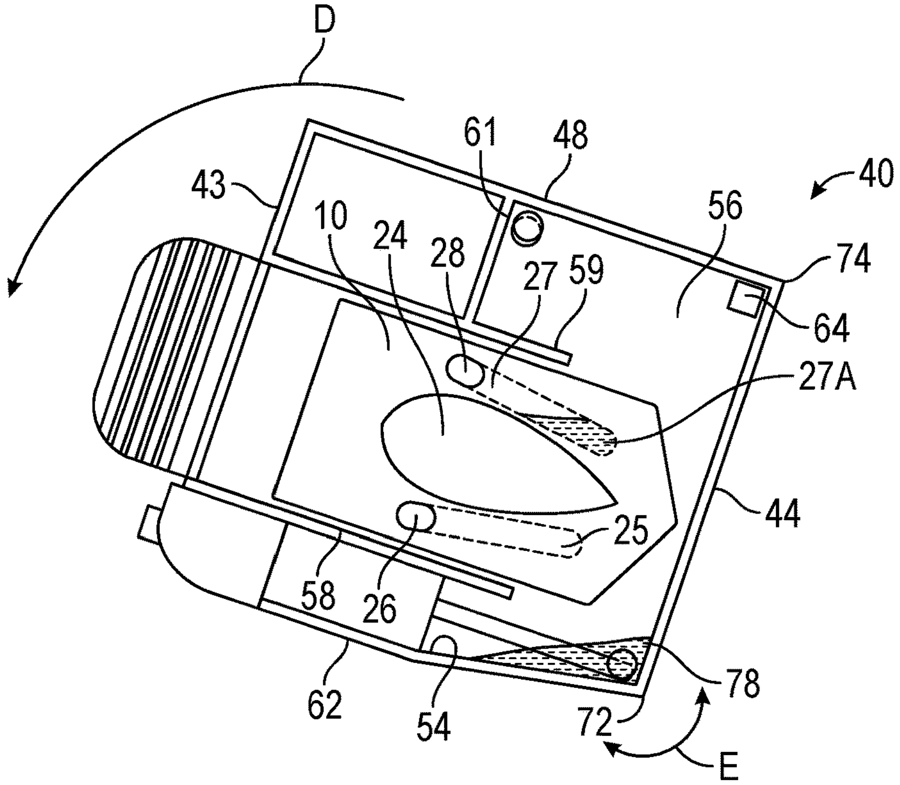

As depicted in FIG. 10D, once the first detectable response is detected and measured in the second corner 74, the analytical research kit 40 may then be rotated in a counter-clockwise direction (as shown by solid directional arrow D) such that the first reaction mixture 76 is transported via gravity from the second corner 74 to the first corner 72 of the reaction chamber 56. The counter-clockwise rotation is to an angle sufficient to dispense the second liquid reagent 25A from the second cavity 25 via the second cavity opening 26 (such angle not being sufficient to dispense the third liquid reagent 27A from the third cavity 27). The second liquid reagent 25A and the first reaction mixture 76 may then be mixed, for example, via agitation and/or oscillation (as shown by arrow E), thereby forming a second reaction mixture 78. Additionally, the analytical research kit 40 can be maintained in a stationary position for a predetermined period of time, as described above.

Figure 10E:
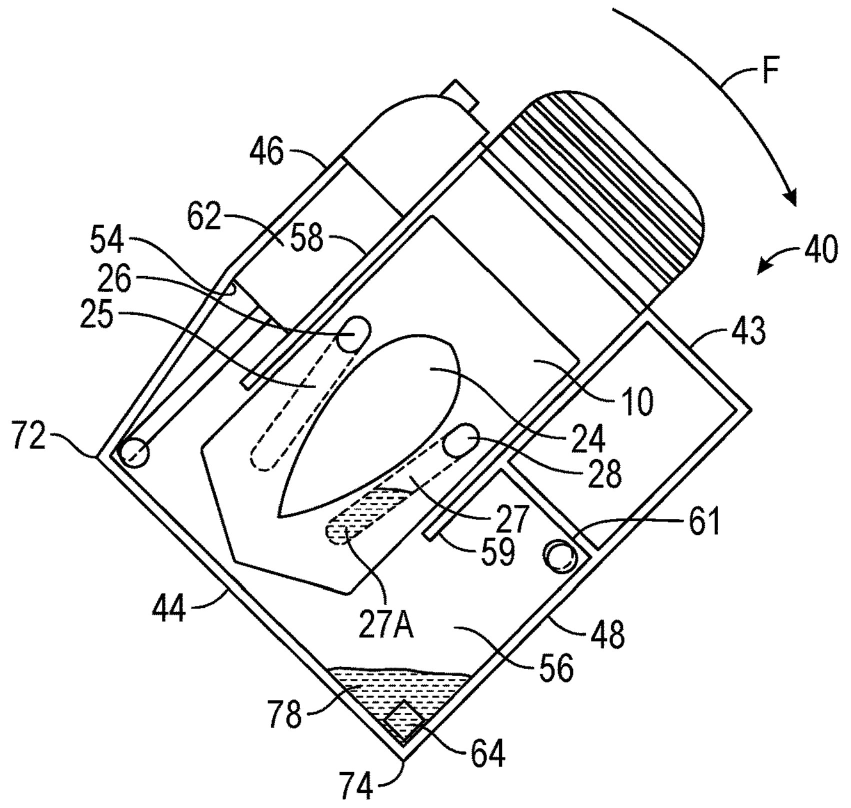

As shown in FIG. 10E, the analytical research kit may then be rotated clockwise (as shown by solid directional arrow F) such that the second reaction mixture 78 is transported via gravity from the first corner 72 to the sample read window 64 in the second corner 74, provided that, in one embodiment, the angle of this rotation is not sufficient to dispense the third liquid reagent 27A from the third cavity 27. Any such second detectable response provided by the second reaction mixture 78 can then be measured, and the remaining assay steps, if necessary, can be carried out subsequent thereto. By way of example only and not by way of limitation, the second detectable response may be a glycated hemoglobin (HbA1c) measurement where the liquid test sample is whole blood, for example, such as when performing an assay for the percent of glycated hemoglobin (HbA1c) in a whole blood sample. In the case of a lipid-based assay, the second detectable response may be a high-density lipoprotein (HDL) cholesterol measurement where the liquid test sample is blood serum, for example, when performing an assay for the calculation of the percent of low-density lipoprotein (LDL) cholesterol present in a blood serum sample.

Figure 10F:
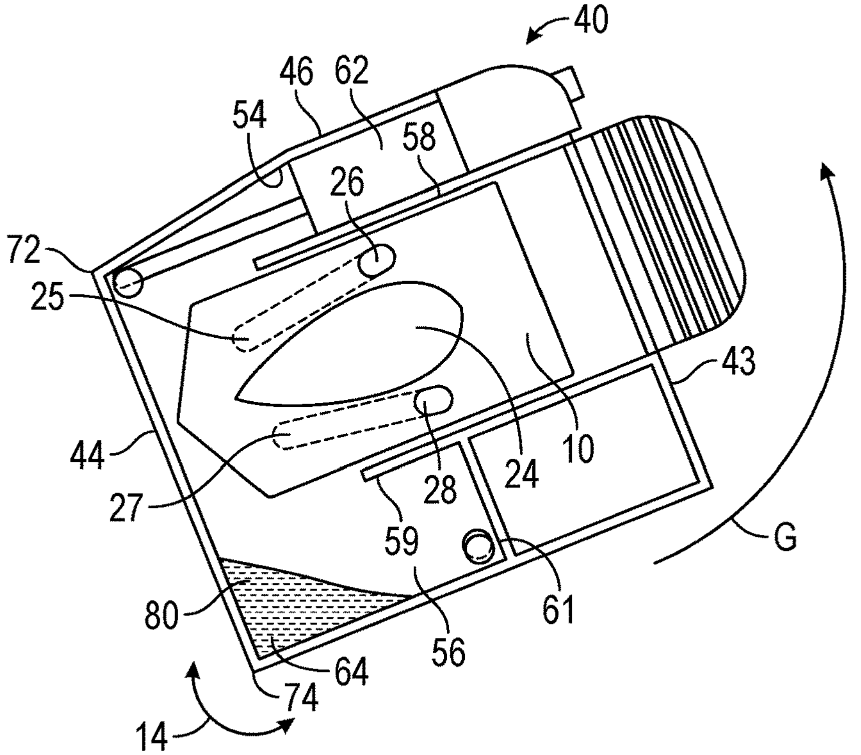

As shown in FIG. 10F, once the second detectable response is detected and measured in the second corner 74, the analytical research kit 40 may then rotated in a clockwise direction (as shown by solid directional arrow G) such that the third liquid reagent 27A is dispensed from the third cavity 27 via the third cavity opening 28. The third liquid reagent 27A and the second reaction mixture 78 may then be mixed, for example, via agitation and/or oscillation (as shown by arrow G), thereby forming a third reaction mixture 80. Additionally, the analytical research kit 40 can be maintained in a stationary position for a predetermined period of time, as described above. As the third reaction mixture 80 is already over the sample read window 64 in the second corner 74, no additional rotation of the analytical research kit 40 is required to obtain an additional measurement. Any such third detectable response provided by the third reaction mixture 80 can then be measured, and the remaining assay steps, if necessary, can be carried out subsequent thereto. By way of example only and not by way of limitation, the third detectable response may be a triglycerides measurement where the liquid test sample is blood serum, for example, such as when performing an assay for the calculation of the percent of low-density lipoprotein (LDL) cholesterol present in a blood serum sample.

Non-Limiting Examples of the Inventive Concept(s)

A liquid analytical reagent dispensing apparatus, the apparatus comprising:

a container having a first end, a second end, a first side, a second side, a bottom side, a top side, a first cavity being open at the top side of the container, a flange extending around the open top of the first cavity, and a second cavity being open near the second end of the container; a first liquid reagent disposed within the first cavity; a second liquid reagent disposed within the second cavity; and a flexible cover removably affixed to the flange of the container to seal the first liquid reagent in the first cavity, the second liquid reagent in the second cavity, and to permit the first liquid reagent to flow from the first cavity, while the second liquid reagent is contained in the second cavity upon removal of the flexible cover from the flange and with the first end of the container positioned substantially vertically beneath the second end of the container.

The apparatus, wherein the apparatus further comprises a third cavity being open near the second end of the container, further wherein a third liquid reagent is disposed within the third cavity.

The apparatus, wherein the second cavity and the third cavity are positioned on opposing sides of the first cavity.

The apparatus, wherein the container has a longitudinal axis extending between the first end and the second end, and wherein each of the second cavity and the third cavity is elongated and parallel to the longitudinal axis.

The apparatus, wherein the container has a longitudinal axis extending between the first end and the second end, and wherein each of the second cavity and the third cavity is elongated and angled relative to the longitudinal axis.

The apparatus, wherein the second cavity and the third cavity are positioned on opposing sides of the first cavity, wherein the second cavity angles away from the first cavity from the first end to the second end, and wherein the third cavity angles away from the first cavity from the first end to the second end.

The apparatus, wherein the apparatus further comprises at least one first support and at least one second support. The apparatus wherein the at least one first support is shorter than the at least one second support.

The apparatus, wherein the first end of the container is angled to form an apex, wherein the apex extends longitudinally from a point of liquid discharge of the first cavity.

The apparatus, wherein the first liquid reagent and the second liquid reagent are the same chemical composition.

The apparatus, wherein the first liquid reagent and the second liquid reagent are different in chemical composition.

The apparatus, wherein the first liquid reagent, the second liquid reagent, and the third liquid reagent are the same chemical composition.

The apparatus, wherein the first liquid reagent, the second liquid reagent, and the third liquid reagent are different in chemical composition.

An analytical reaction kit, the kit comprising: a reaction cassette, the reaction cassette comprising: a body, the body comprising a top perimeter side, a bottom perimeter side, a first perimeter side, a second perimeter side, a bottom portion, and a top portion thereby forming a reaction cassette chamber; an inlet for introducing a liquid test sample into the reaction cassette chamber; and a reaction chamber in liquid communication with the inlet; a liquid analytical reagent dispensing apparatus, the apparatus comprising: a container having a first end, a second end, a first side, a second side, a bottom side, a top side, a first cavity being open at the top side of the container, a flange extending around the open top of the first cavity, and a second cavity being open near the second end of the container; a first liquid reagent disposed within the first cavity; a second liquid reagent disposed within the second cavity; and a flexible cover removably affixed to the flange of the container to seal the first liquid reagent in the first cavity, the second liquid reagent in the second cavity, and to permit the first liquid reagent to flow from the first cavity, while the second liquid reagent is contained in the second cavity upon removal of the flexible cover from the flange and with the first end of the container positioned substantially vertically beneath the second end of the container; and a capillary, the capillary capable of being partially inserted into the inlet of the reaction cassette to thereby introduce a liquid test sample into the reaction chamber.

The kit, wherein the reaction cassette further comprises at least one solid reagent zone positioned along the reaction chamber, the solid reagent zone comprising a solid analytical reagent.

The kit, wherein the liquid analytical reagent dispensing apparatus further comprises a third cavity in which a third liquid reagent is disposed.

The kit, wherein the first liquid reagent and the second liquid reagent are the same chemical composition.

The kit, wherein the first liquid reagent and the second liquid reagent are different in chemical composition.

The kit, wherein the first liquid reagent, the second liquid reagent, and the third liquid reagent are the same chemical composition.

The kit, wherein the first liquid reagent, the second liquid reagent, and the third liquid reagent are different in chemical composition.

A method for performing analytical reactions to determine the presence of an analyte in a liquid test sample, the method comprising the steps of: providing a reaction cassette having a substantially horizontal axis of rotation, the reaction cassette comprising: a body, the body comprising a top perimeter side, a bottom perimeter side, a first perimeter side, a second perimeter side, bottom portion, and a top portion thereby forming a reaction cassette chamber; an inlet for introducing a liquid test sample into the reaction cassette chamber; a reaction channel in liquid communication with the inlet; and a liquid analytical reagent dispensing apparatus incorporated into the reaction cassette, the apparatus comprising: a container having a first end, a second end, a first side, a second side, a bottom side, a top side, a first cavity being open at the top side of the container, a flange extending around the open top of the first cavity, and a second cavity being open near the second end of the container; a first liquid reagent disposed within the first cavity; a second liquid reagent disposed within the second cavity; and a flexible cover removably affixed to the flange of the container to seal the first liquid reagent in the first cavity and the second liquid reagent in the second cavity and to permit the first liquid reagent to flow from the first cavity, while the second liquid reagent is contained in the second cavity upon removal of the flexible cover from the flange and with the first end of the container positioned substantially vertically beneath the second end of the container; introducing the liquid test sample via the inlet of the reaction cassette into the reaction chamber; removing the flexible cover thereby introducing the first liquid reagent from the first cavity into the reaction channel, whereby the first liquid reagent mixes with the liquid test sample to thereby form a first liquid reaction mixture in the reaction channel; measuring a detectable response in the first reaction mixture to determine the presence of at least one analyte present in the first reaction mixture; rotating the reaction cassette about the horizontal axis such that the second liquid reagent is introduced from the second cavity into the reaction channel; oscillating the reaction cassette about such horizontal axis to agitate the first reaction mixture so as to mix the first reaction mixture with the second liquid reagent thereby forming a second reaction mixture; and measuring a detectable response in the second reaction mixture to determine the presence of at least one analyte present in the second reaction mixture.

The method, wherein the liquid analytical reagent dispensing apparatus further comprises a third cavity in which a third liquid reagent is disposed.

The method, wherein the method comprises a step of rotating the reaction cassette about the horizontal axis such that the third liquid reagent is introduced from the third cavity into the reaction channel.

The method, wherein the method comprises a step of oscillating the second reaction mixture with the third liquid reagent to thereby form a third reaction mixture.

The method, wherein the method comprises a step of measuring a detectable response in the third reaction mixture to determine the presence of at least one analyte in the third reaction mixture.

The method, wherein a concentration of at least one analyte present in the liquid test sample is detected via the measurement.

Thus, in accordance with the presently disclosed and claimed inventive concept(s), there have been provided devices, kits, and methods for dispensing at least two liquid reagents for use in analyte(s) detection assays. As described herein, the presently disclosed and claimed inventive concept(s) relate to embodiments of a modified apparatus present within a reaction cassette that is capable of dispensing at least two liquid reagents for use in analyte(s) detection assays, as well as kits and methods of use related thereto. Is created that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A liquid analytical reagent dispensing apparatus, the apparatus comprising:

- a container having a first end, a second end, a first side, a second side, a bottom side, a top side, a first cavity being open at the top side of the container, a flange extending around the open top of the first cavity, and a second cavity being open near the second end of the container;
- a first liquid reagent disposed within the first cavity;
- a second liquid reagent disposed within the second cavity; and
- a single flexible cover removably affixed to the flange of the container to seal the first liquid reagent in the first cavity and the second liquid reagent in the second cavity, wherein upon complete removal of the single flexible cover from the flange, the first liquid reagent flows from the first cavity, while the second liquid reagent remains and is contained in the opened second cavity when the container is oriented such that the first end of the container is positioned substantially vertically beneath the second end of the container.

2. The apparatus of claim 1, wherein the apparatus further comprises a third cavity being open near the second end of the container, further wherein a third liquid reagent is disposed within the third cavity.

3. The apparatus of claim 2, wherein the second cavity and the third cavity are positioned on opposing sides of the first cavity.

4. The apparatus of claim 3, wherein a longitudinal axis extends between the first end and the second end of the container, and wherein each of the second cavity and the third cavity is elongated and oriented substantially parallel to the longitudinal axis.

5. The apparatus of claim 3, wherein a longitudinal axis extends between the first end and the second end of the container, and wherein each of the second cavity and the third cavity is elongated and angled relative to the longitudinal axis.

6. The apparatus of claim 2, wherein the second cavity and the third cavity are positioned on opposing sides of the first cavity, wherein the second cavity angles away from the first cavity from the first end to the second end of the container, and wherein the third cavity angles away from the first cavity from the first end to the second end of the container.

7. The apparatus of claim 1, wherein the apparatus further comprises at least one support.

8. The apparatus of claim 7, wherein the apparatus comprises a first support and a second support, wherein the first support is shorter than the second support.

9. The apparatus of claim 1, wherein the first end of the container is angled to form an apex, wherein the apex extends longitudinally from a point of liquid discharge of the first cavity.

10. The apparatus of claim 1, wherein the first liquid reagent and the second liquid reagent are the same chemical composition.

11. The apparatus of claim 1, wherein the first liquid reagent and the second liquid reagent are different in chemical composition.

12. The apparatus of claim 2, wherein the first liquid reagent, the second liquid reagent, and the third liquid reagent are the same chemical composition.

13. The apparatus of claim 2, wherein the first liquid reagent, the second liquid reagent, and the third liquid reagent are different in chemical composition.

14. An analytical reaction kit, the kit comprising:

a reaction cassette, the reaction cassette comprising:

a body, the body comprising a top perimeter side, a bottom perimeter side, a first perimeter side, a second perimeter side, a bottom portion, and a top portion thereby forming a reaction cassette chamber;

an inlet for introducing a liquid test sample into the reaction cassette chamber; and a reaction chamber in liquid communication with the inlet;

a liquid analytical reagent dispensing apparatus, the apparatus comprising:

a container having a first end, a second end, a first side, a second side, a bottom side, a top side, a first cavity being open at the top side of the container, a flange extending around the open top of the first cavity, and a second cavity being open near the second end of the container;

a first liquid reagent disposed within the first cavity;

a second liquid reagent disposed within the second cavity; and a single flexible cover removably affixed to the flange of the container to seal the first liquid reagent in the first cavity and the second liquid reagent in the second cavity, wherein upon complete removal of the single flexible cover from the flange, the first liquid reagent flows from the first cavity, while the second liquid reagent remains and is contained in the opened second cavity when the container is oriented such that the first end of the container is positioned substantially vertically beneath the second end of the container; and a capillary, the capillary capable of being partially inserted into the inlet of the reaction cassette to thereby introduce a liquid test sample into the reaction chamber.

15. The kit of claim 14, wherein the reaction cassette further comprises at least one solid reagent zone positioned along the reaction chamber, the solid reagent zone comprising at least one solid analytical reagent.

16. The kit of claim 14, wherein the liquid analytical reagent dispensing apparatus further comprises a third cavity being open near the second end of the container, further wherein a third liquid reagent is disposed within the third cavity.

17. The kit of claim 14, wherein the first liquid reagent and the second liquid reagent are the same chemical composition.

18. The kit of claim 14, wherein the first liquid reagent and the second liquid reagent are different in chemical composition.

19. The kit of claim 16, wherein the first liquid reagent, the second liquid reagent, and the third liquid reagent are the same chemical composition.

20. The kit of claim 16, wherein the first liquid reagent, the second liquid reagent, and the third liquid reagent are different in chemical composition.

21. A method for performing analytical reactions to determine the presence of an analyte in a liquid test sample, the method comprising the steps of:

providing a reaction cassette having a substantially horizontal axis of rotation, the reaction cassette comprising:

a body, the body comprising a top perimeter side, a bottom perimeter side, a first perimeter side, a second perimeter side, bottom portion, and a top portion thereby forming a reaction cassette chamber;

an inlet for introducing a liquid test sample into the reaction cassette chamber;

a reaction channel in liquid communication with the inlet; and a liquid analytical reagent dispensing apparatus incorporated into the reaction cassette, the apparatus comprising:

a container having a first end, a second end, a first side, a second side, a bottom side, a top side, a first cavity being open at the top side of the container, a flange extending around the open top of the first cavity, and a second cavity being open near the second end of the container;

a first liquid reagent disposed within the first cavity;

a second liquid reagent disposed within the second cavity; and a single flexible cover removably affixed to the flange of the container to seal the first liquid reagent in the first cavity and the second liquid reagent in the second cavity, wherein upon complete removal of the single flexible cover from the flange, the first liquid reagent flows from the first cavity, while the second liquid reagent remains and is contained in the opened second cavity the first end of the container is positioned substantially vertically beneath the second end of the container;

introducing the liquid test sample via the inlet of the reaction cassette into the reaction chamber;

removing the single flexible cover thereby introducing the first liquid reagent from the first cavity into the reaction channel, whereby the first liquid reagent mixes with the liquid test sample to thereby form a first reaction mixture in the reaction channel;

measuring a detectable response in the first reaction mixture to determine the presence of at least one analyte present in the first reaction mixture;

rotating the reaction cassette about the horizontal axis such that the second liquid reagent is selectively introduced from the second cavity into the reaction channel;

oscillating the reaction cassette about such horizontal axis to agitate the first liquid reaction mixture so as to mix the first reaction mixture with the second liquid reagent thereby forming a second reaction mixture; and measuring a detectable response in the second reaction mixture to determine the presence of at least one analyte present in the second reaction mixture.

22. The method of claim 21, wherein the liquid analytical reagent dispensing apparatus further comprises a third cavity being open near the second end of the container, further wherein a third liquid reagent is disposed within the third cavity.

23. The method of claim 22, wherein the method comprises a step of rotating the reaction cassette about the horizontal axis such that the third liquid reagent is selectively introduced from the opened third cavity into the reaction channel.

24. The method of claim 23, wherein the method comprises a step of oscillating the second reaction mixture with the third liquid reagent to thereby form a third reaction mixture.

25. The method of claim 24, wherein the method comprises a step of measuring a detectable response in the third reaction mixture to determine the presence of at least one analyte in the third reaction mixture.

26. The method of claim 21, wherein a concentration of at least one analyte present in the liquid test sample is detected via the measurement.

* * * * *